US00PP21309P2

(12) United States Plant Patent
Eveleens

(10) Patent No.: US PP21,309 P2
(45) Date of Patent: Sep. 21, 2010

(54) ***GERBERA* PLANT NAMED 'FLOMITE'**
(50) Latin Name: *Gerbera jamesonii*
Varietal Denomination: Flomite

(75) Inventor: Jan Leendert Eveleens, Aalsmeer (NL)

(73) Assignee: Florist de Kwakel B.V., Aalsmeer (NL)

( * ) Notice: Subject to any disclaimer, the term of this patent is extended or adjusted under 35 U.S.C. 154(b) by 0 days.

(21) Appl. No.: 12/454,016

(22) Filed: May 11, 2009

(51) Int. Cl.
*A01H 5/00* (2006.01)

(52) U.S. Cl. ..... Plt./357
(58) Field of Classification Search ..... Plt./357
See application file for complete search history.

*Primary Examiner*—June Hwu
(74) *Attorney, Agent, or Firm*—C. A. Whealy

(57) ABSTRACT

A new and distinct cultivar of *Gerbera* plant named 'Flomite', characterized by its compact, upright and uniformly mounding plant habit; freely flowering habit; semi-double type inflorescences with ray florets that are orange red in color; and upright, strong and relatively short scapes.

1 Drawing Sheet

Botanical designation: *Gerbera jamesonii.*
Cultivar denomination: 'FLOMITE'.

BACKGROUND OF THE INVENTION

The present invention relates to a new and distinct cultivar of *Gerbera* plant, botanically known as *Gerbera jamesonii* and hereinafter referred to by the name 'Flomite'.

The new *Gerbera* plant is a product of a planned breeding program conducted by the Inventor in De Kwakel, The Netherlands. The objective of the breeding program is to create new compact container *Gerbera* cultivars with numerous inflorescences, good garden performance and attractive ray and disc floret coloration.

The new *Gerbera* plant originated from a cross-pollination in March, 2003 in De Kwakel, The Netherlands of *Gerbera jamesonii* 'Fabio'×'Cosmo', not patented, as the female, or seed, parent with *Gerbera jamesonii* 'Autumn', not patented, as the male, or pollen, parent. The new *Gerbera* was discovered and selected by the Inventor as a single flowering plant within the progeny of the stated cross-pollination in a controlled greenhouse environment in De Kwakel, The Netherlands during the spring of 2004.

Asexual reproduction of the new *Gerbera* plant by tissue culture in a controlled environment in De Kwakel, The Netherlands since the summer of 2004 has shown that the unique features of this new *Gerbera* plant are stable and reproduced true to type in successive generations.

SUMMARY OF THE INVENTION

Plants of the new *Gerbera* have not been observed under all possible environmental conditions. The phenotype may vary somewhat with variations in environment such as temperature and light intensity, without, however, any variance in genotype.

The following traits have been repeatedly observed and are determined to be the unique characteristics of 'Flomite'. These characteristics in combination distinguish 'Flomite' as a new and distinct cultivar of *Gerbera:*

1. Compact, upright and uniformly mounding plant habit.
2. Freely flowering habit.
3. Semi-double type inflorescences with ray florets that are orange red in color.

4. Upright, strong and relatively short scapes.

Plants of the new *Gerbera* differ from plants of the female parent, 'Fabio'×'Cosmo', in the following characteristics:

1. Plants of the new *Gerbera* are more compact than plants of 'Fabio'×'Cosmo'.
2. Plants of the new *Gerbera* have shorter scapes than plants of 'Fabio'×'Cosmo'.
3. Ray florets of plants of the new *Gerbera* are orange red in color whereas ray florets of plants of 'Fabio'× 'Cosmo' are yellow in color.

Plants of the new *Gerbera* differ from plants of the male parent, 'Autumn', in the following characteristics:

1. Plants of the new *Gerbera* are more compact than plants of 'Autumn'.
2. Plants of the new *Gerbera* have shorter scapes than plants of 'Autumn'.
3. Ray florets of plants of the new *Gerbera* are orange red in color whereas ray florets of plants of 'Autumn' are orange in color.

Plants of the new *Gerbera* can be compared to plants of the *Gerbera jamesonii* 'Everlast Carmine', not patented. Plants of the new *Gerbera* differ from plants of 'Everlast Carmine' in the following characteristics:

1. Plants of the new *Gerbera* are more uniform in growth habit than plants of 'Everlast Carmine'.
2. Plants of the new *Gerbera* have larger inflorescences than plants of 'Everlast Carmine'.
3. Plants of the new *Gerbera* have semi-double type inflorescences whereas plants of 'Everlast Carmine' have single type inflorescences.
4. Ray florets of plants of the new *Gerbera* are red orange in color whereas ray florets of plants of 'Everlast Carmine' are dark red in color.
5. Plants of the new *Gerbera* have thicker scapes than plants of 'Everlast Carmine'.

BRIEF DESCRIPTION OF THE PHOTOGRAPH

The accompanying photograph illustrates the overall appearance of the new *Gerbera* plant. This photograph shows the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Flomite' grown in a container.

DETAILED BOTANICAL DESCRIPTION

The aforementioned photograph and following observations and measurements describe plants grown in a glass-covered greenhouse during the winter in De Kwakel, The Netherlands and under conditions and practices which approximate those generally used in commercial container *Gerbera* production. During the production of the plants, day temperatures ranged from 19° C. to 26° C. and night temperatures ranged from 16° C. to 18° C. Rooted young tissue-cultured plants were planted in 19-cm containers and had been growing for six months when the photograph and description were taken. In the following description, color references are made to The Royal Horticultural Society Colour Chart, Fifth Edition, 2007, except where general terms of ordinary dictionary significance are used.

Botanical classification: *Gerbera jamesonii* 'Flomite'.

Parentage:

*Female, or seed, parent.*—*Gerbera jamesonii* 'Fabio'× 'Cosmo', not patented.

*Male, or pollen, parent.*—*Gerbera jamesonii* 'Autumn', not patented.

Propagation:

*Type.*—By tissue culture.

*Time to initiate roots.*—About 2.5 weeks at temperatures of 20° C.

*Time to produce a rooted young plant.*—About five to six weeks at temperatures of 20° C. to 26° C.

*Root description.*—Fibrous; white in color.

*Rooting habit.*—Moderate branching; dense.

Plant description:

*Appearance.*—Herbaceous semi-double type *Gerbera;* compact, upright and uniformly mounding plant habit; arching leaves arranged in basal rosettes; dense and bushy habit; moderately vigorous growth habit.

*Plant height.*—About 63.8 cm.

*Plant width.*—About 69.9 cm.

Foliage description:

*Arrangement.*—Alternate, simple.

*Length.*—About 30.4 cm.

*Width.*—About 12.6 cm.

*Shape.*—Runcinate; lanceolate to narrowly elliptic in outline.

*Apex.*—Obtuse.

*Base.*—Acuminate.

*Margin.*—Pinnately lobed with coarse and irregular sinuses, lobes divergent; undulate.

*Texture, upper surface.*—Sparsely pubescent.

*Texture, lower surface.*—Moderately pubescent; woolly.

*Venation pattern.*—Pinnate.

*Color.*—Developing leaves, upper surface: Between 141A and 143A. Developing leaves, lower surface: Between 137D and 138B. Fully expanded leaves, upper surface: Close to N137A; venation, close to 144A. Fully expanded leaves, lower surface: Close to 138A to 138B; venation, close to 144B to 144C.

*Petioles.*—Length: About 9.8 cm. Diameter: About 5.5 mm. Texture, upper surface: Sparsely pubescent. Texture, lower surface: Moderately pubescent. Color, upper surface: Close to 148A. Color, lower surface: Close to 144A flushed with close to 148A.

Inflorescence description:

*Appearance.*—Semi-double type inflorescence form with narrowly oblanceolate to narrowly elliptic-shaped ray florets; solitary inflorescences borne on upright, strong and relatively short scapes above the foliar plane; ray and disc florets arranged acropetally on a capitulum.

*Fragrance.*—None detected.

*Flowering season.*—Plants begin flowering about four months after planting and flower from early spring to the end of the summer in outdoor gardens in The Netherlands. Plants flower year-round under greenhouse conditions.

*Inflorescence longevity.*—Inflorescences last about two weeks on the plant; inflorescences persistent.

*Quantity of inflorescences.*—Freely flowering habit with about eight open and developing inflorescences per plant at one time.

*Inflorescence bud.*—Height: About 1.8 cm. Diameter: About 2.7 cm. Shape: Oblate. Color: Close to 144C.

*Inflorescence size.*—Diameter: About 11.4 cm. Depth (height): About 3 cm. Diameter of disc: About 4.3 cm. Receptacle height: About 6 mm. Receptacle diameter: About 8 mm. Receptacle color: Close to 155C.

*Ray florets.*—Orientation: Initially upright, then about 75° from vertical. Length: About 5.1 cm. Width: About 1.3 cm. Shape: Narrowly oblanceolate to narrowly elliptic. Apex: Emarginate. Base: Cuneate. Margin: Entire. Texture, upper and lower surfaces: Smooth, glabrous; longitudinally ridged. Number of ray florets per inflorescence: About 100 arranged in about three whorls. Color: When opening, upper surface: Close to 33A. When opening, lower surface: Close to 29A; longitudinal stripes, close to 14D. Fully opened, upper surface: Close to 33A. Fully opened, lower surface: Close to 18A.

*Disc florets.*—Arrangement: Massed at center of receptacle. Shape: Tubular, fused. Apex: Acute. Base: Fused. Margin: Entire. Length: About 1.7 cm. Width: About 5 mm. Texture, upper and lower surfaces: Smooth, glabrous. Number of disc florets per inflorescence: About 500. Color, immature: Apex: Close to 42A. Mid-section and base: Close to 29A. Color, mature: Apex: Close to 23A. Mid-section and base: Close to 18A.

*Pappus.*—Quantity per floret: About 50. Length: About 8 mm. Diameter: Less than 1 mm. Texture: Soft. Color: Close to 187A.

*Phyllaries.*—Number of phyllaries per inflorescence: About 120 in about four whorls. Length: About 1.3 cm. Width: About 3 mm. Shape: Lanceolate. Apex: Acute. Base: Cuneate. Margin: Entire. Texture, upper surface: Smooth, glabrous. Texture, lower surface: Densely tomentose. Color, upper surface: Close to 143A; apices, close to 144A. Color, lower surface: Close to 137B.

*Scapes.*—Length: About 46.3 cm. Diameter: About 8 mm. Angle: Erect. Strength: Strong. Texture: Densely tomentose. Color: Close to 144A to 144B; towards the apex, close to 137D.

*Reproductive organs.*—Androecium: (present on disc florets only) Quantity per floret: Two. Filament length: About 7 mm. Filament color: Close to 155A.

Anther shape: Lanceolate. Anther length: About 4 mm. Anther color: Close to 12B. Pollen amount: Moderate. Pollen color: Close to 12A. Gynoecium: (present on ray and disc florets) Quantity per floret: One. Pistil length: About 1.4 cm. Stigma shape: Rounded; curved. Stigma color: Close to 10C. Style length: About 1.3 cm. Style color: Close to 10D; towards the base, close to 155A. Ovary color: Close to 4D.

*Seed/fruit.*—Seed and fruit production has not been observed.

Disease/pest resistance: Resistance to pathogens and pests common to *Gerberas* has not been observed on plants of the new *Gerbera* grown under commercial conditions.

Temperature tolerance: Plants of the new *Gerbera* have been observed to tolerate temperatures from about 1° C. to about 35° C.

It is claimed:

1. A new and distinct *Gerbera* plant named 'Flomite' as illustrated and described.

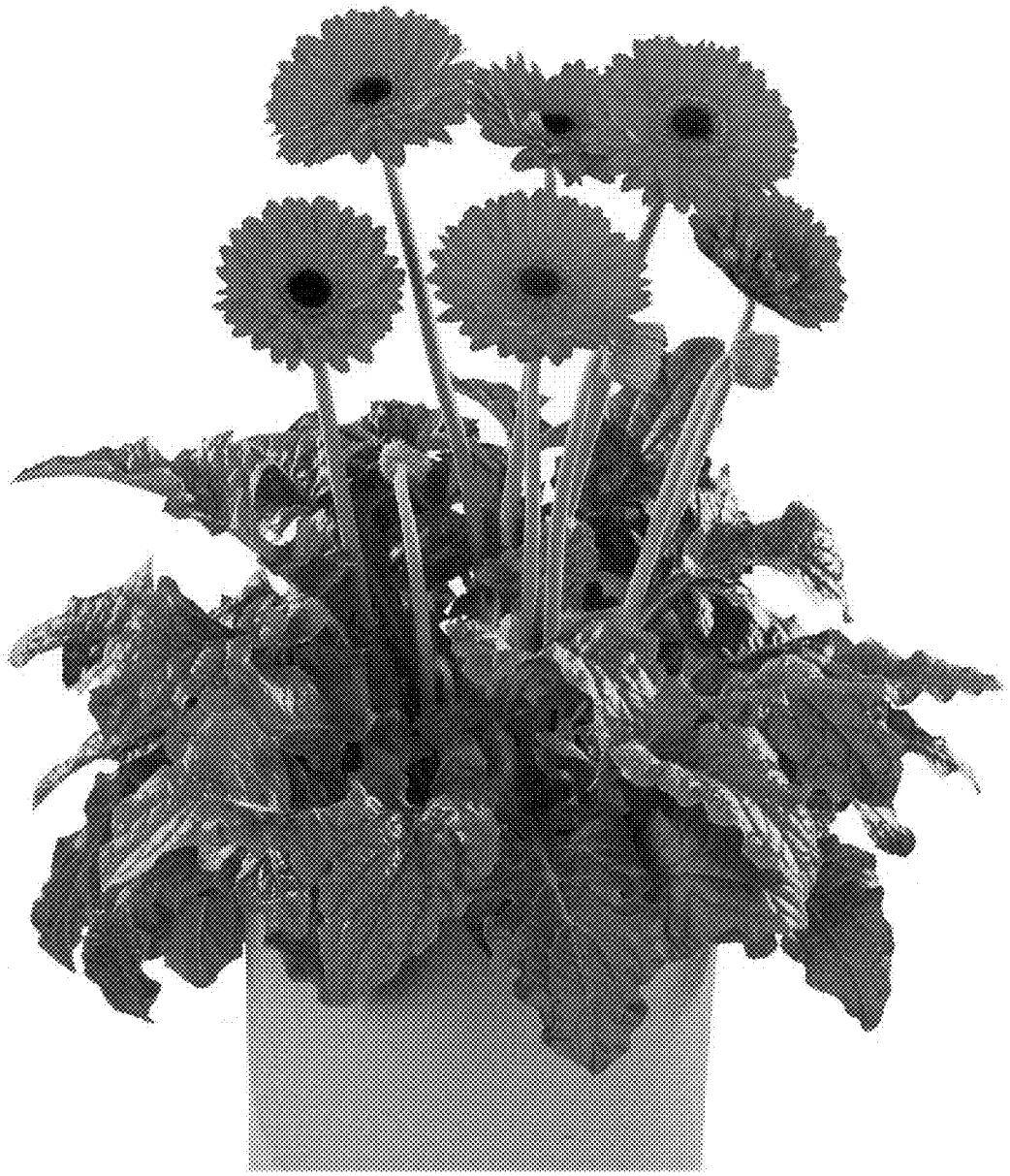

* * * * *